(12) United States Patent
Chen

(10) Patent No.: US 6,448,545 B1
(45) Date of Patent: Sep. 10, 2002

(54) PRECISION ENDOSCOPIC IMAGING SYSTEM

(75) Inventor: Min Chen, Brookline, MA (US)

(73) Assignee: Syncrotronics Corp., Chestnut Hill, MA (US)

( * ) Notice: Subject to any disclaimer, the term of this patent is extended or adjusted under 35 U.S.C. 154(b) by 0 days.

(21) Appl. No.: 09/483,005

(22) Filed: Jan. 18, 2000

Related U.S. Application Data

(63) Continuation-in-part of application No. 09/254,959, filed as application No. PCT/US96/19213 on Dec. 3, 1996.

(51) Int. Cl.[7] .................................................. H01J 40/14
(52) U.S. Cl. ............................. 250/214 VT; 250/214.1; 250/208.1
(58) Field of Search ............................. 250/207, 208.1, 250/214 VT, 310, 332, 336.1, 214.1

(56) References Cited

U.S. PATENT DOCUMENTS

| | | |
|---|---|---|
| 4,422,091 A | 12/1983 | Liu |
| 4,633,076 A | 12/1986 | Butterwick |
| 4,995,396 A | 2/1991 | Inaba et al. |
| 5,381,000 A | 1/1995 | McKee, Jr. |

FOREIGN PATENT DOCUMENTS

| | | |
|---|---|---|
| DE | 3437203 | 10/1984 |
| EP | 87202369.2 | 11/1987 |
| EP | 95308444.9 | 11/1995 |
| WO | PCT/US93/07205 | 7/1993 |
| WO | PCT/GB94/02301 | 10/1994 |

OTHER PUBLICATIONS

*Stereo X–ray Imaging using a single Multiple–Source X–ray Detector*, Min chen et al.
*A high–resolution detector based on liquid–core scintillating fibres with readout via an electron–bombarded charge–coupled device*, C. Cianfarani et al.

*Primary Examiner*—Stephone Allen
(74) *Attorney, Agent, or Firm*—Stephen G. Matzuk

(57) ABSTRACT

An imaging system is disclosed for use in low-light environments or environments where low-levels of such radiation is desirable. Examples of such environments are endoscopy, laparoscopy, mammography and night photography. In the case of radiation that is other than visible light, a radiation converter and method for fabricating same is disclosed. The radiation converter comprises a film of heavy scintillator (e.g. $CdWO_4$) coated on a fiber optical window to efficiently convert the radiation into visible light. The visible light is passed into a signal amplifier employing a focussing electron-bombarded charge-couple device (FEBCCD) or a focussing electron-bombarded complementary metal-oxide semiconductor (FEBCMOS) to amplify the signal. Novel methods of performing three-dimension imaging using this system as well as removing the effects of high-speed movement are also disclosed.

20 Claims, 9 Drawing Sheets

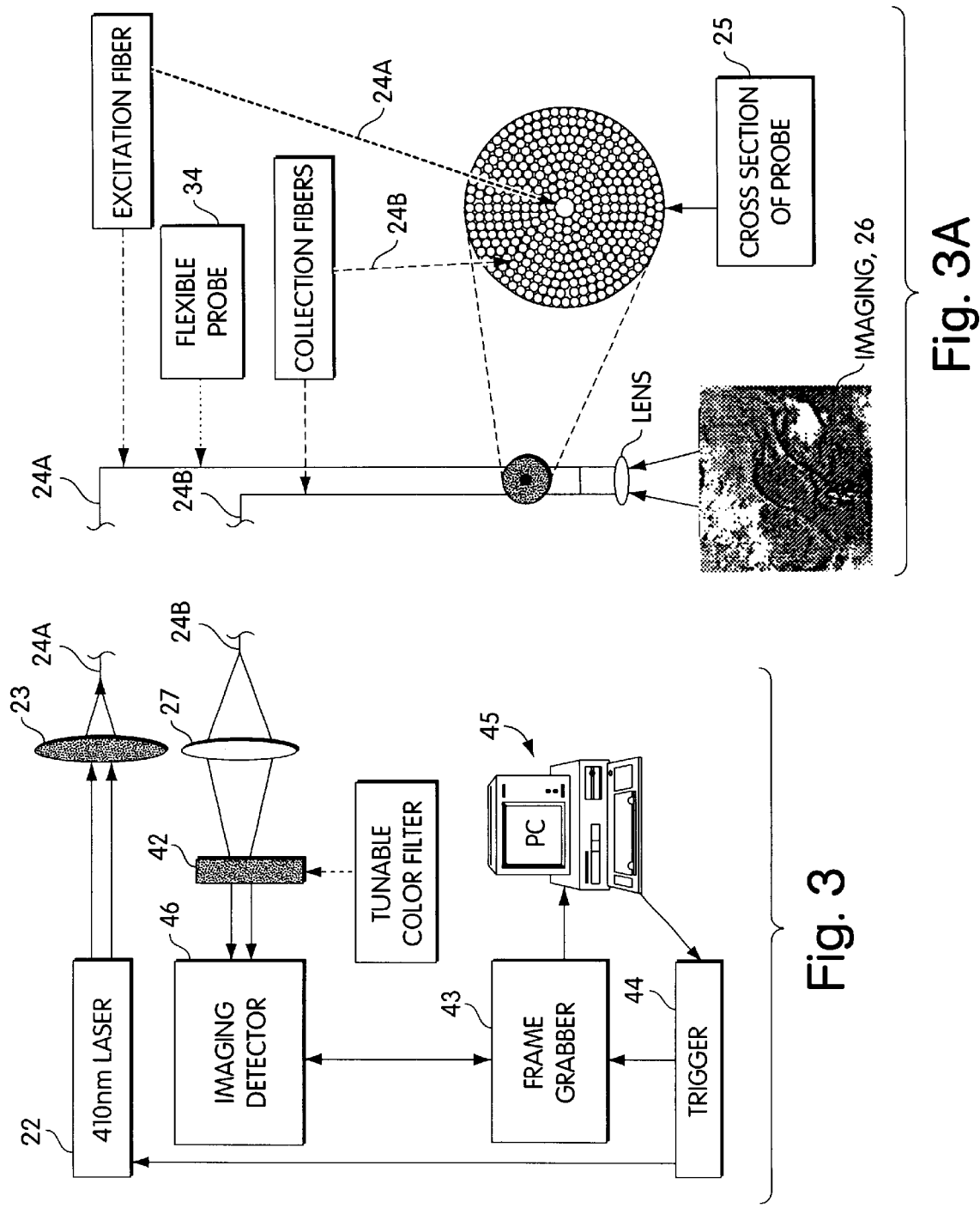

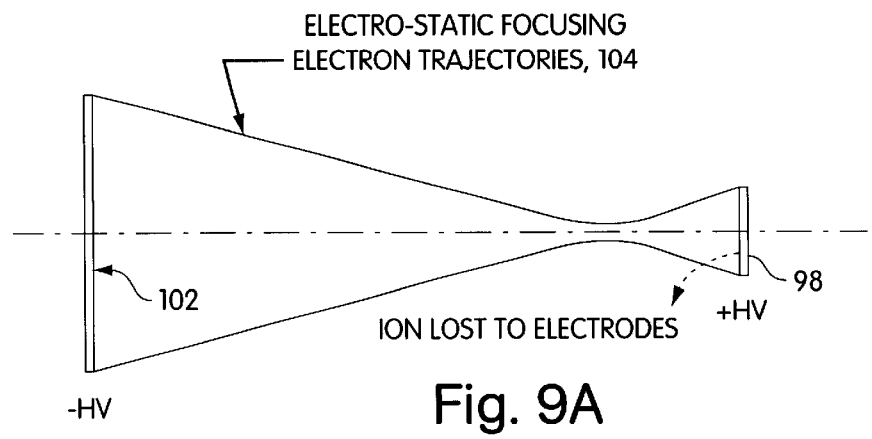
Fig. 9A
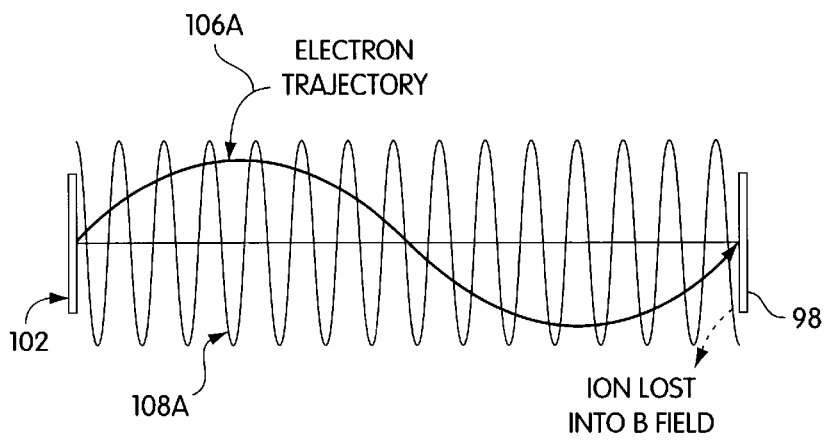 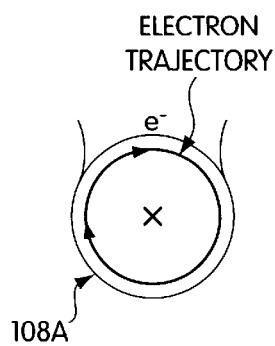
Fig. 10A    Fig. 10B
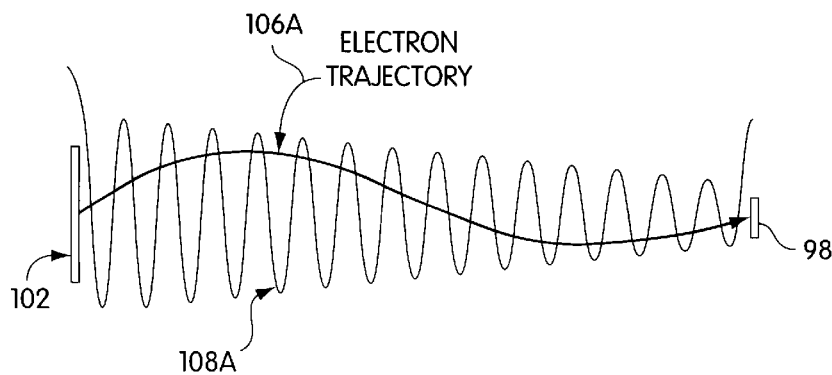 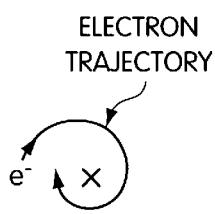
Fig. 11A    Fig. 11B

PRECISION ENDOSCOPIC IMAGING SYSTEM

This application is a Continuation-In-Part of U.S. patent application Ser. No. 09/254,959, which is a national stage filing of PCT/US96/19213, (incorporated by reference.

FIELD OF THE INVENTION

The present invention relates generally to precision imaging systems. More particularly, the invention relates to precision endoscopic (and other, e.g. mammographic) imaging systems that operate at low levels of radiation to form a high-resolution image.

BACKGROUND OF THE INVENTION

In endoscopic imaging systems, high image resolution and high sensitivity (or low radiation). is an important system characteristic. This is particularly true in medical imaging through where the clarity and contrasts within an image directly affect the diagnostic capabilities of a physician. That is, the higher the resolution and the higher the sensitivity, the earlier and easier the detection of abnormalities is. Likewise, industrial uses such as quality control of product components operate in much the same manner and lack of detection of abnormalities can have similarly disastrous results.

Higher resolution images at low radiation levels can also help distinguish aspects of the image thus presenting additional valuable information. For example, if the image shows certain fractal duct structures then a physician may be able to deduce that a tumor is benign. Further, accurate representation of objects in the image, as to image size, for example, assists in diagnosis. That is, the observation of a stable tumor size over time alleviates the fear of malignancies without intrusive and invasive operations.

Applications of fluorescent endoscopy compare tissue regions based upon different image signals for at least two light wavelengths, e.g. red and green images for the same tissue. However, the process is typically limited by detector noise and the rate at which the different color images are provided. The noise is typically at the level of 100 electrons, while the rate of acquiring a red and green image pair is as much as a few hundred milliseconds or more, requiring patient immobilization and mechanically fixed, i.e. tripod-mounted endoscope probes which seriously inhibit the usability of present day fluorescent endoscopes. The latter could be solved by using a pair of photo detectors assemblies for measuring the intensity of light emitted from the tissue at two different wavelengths simultaneously. However, two detectors are clumsy and requires expensive cross-correlation which is costly in time and expense.

A proximity electron bombardment charge-coupled device (EBCCD) has no focussing. To have acceptable resolution, the distance between the EBCCD chip and photocathode must be kept small (0.7–0.8 mm). At this distance, it is impossible to apply high voltage to the elements of the EBCCD. The maximum gain is typically limited to a few hundred. Moreover, positive ions are produced by energetic electrons which after hitting the anode, strike back at the cathode to produce spurious electrons, which: hit the anode again at different positions from the original electron. Such spurious electrons produce noise in the image signal, destroys the image resolution and shorten the life of the EBCCD. Therefore, intensified image CCDs have heretofore included micro-channel-plate (MCP) elements to reduce these noise source. However, the MCP itself is noisy with only about 60% acceptance.

Prior intensified CCD devices all use the (light-spreading) phosphor screen as the transmitting medium and the (noisy and with small acceptance) MCP as the amplification means. All such intensified devices have poor modulate transfer functions (MTF) and poor image quality.

Medical diagnostic imaging systems utilizing x-ray image intensifier tubes are well known in the art. The image intensifier tube has as a component a scintillator that converts an x-ray image, representing the absorption of x-rays by the :structure to be depicted, into visible light. Devices such as this are widely used for medical observation. The visible light can then be made to impinge upon a photographic film or a photosensitive detector that electronically records the image. The film can then be developed for direct review, at the expense of time, or the electronic signals from the detector can be processed and transmitted to a cathode-ray tube ('CRT') or photographic recording system.

FIG. 1 shows a prior art scintillator 10, which is generally formed by depositing cesium iodide by vacuum evaporation onto a substrate 14. The thickness of the cesium iodide, or structured cesium, deposited generally ranges from 150–500 microns. The cesium iodide is deposited in the form of needles 12 each with a diameter of 5–10 microns. Since the refractive index of cesium iodide is 1.8, a fiber optic effect is obtained. This effect minimizes the lateral diffusion of the light within the scintillating material. A scintillator of this type, for example, is described in U.S. Pat. No. 4,803,366 dated Feb. 7, 1989.

The resolution of the image intensifier tube depends on the capacity of the cesium iodide needles 12 to properly channel the light. Non-uniformity (i.e. positions dependent light yield across the needles) and cross talks between the needles can result in large non-Gaussian tails which degrade the spatial image resolution. The cesium iodide as well as another popular material, sodium iodide, used as x-ray converters all have relatively low densities and thus low detective quantum efficiency ("DQE") if a thin layer of scintillator is used, and/or poor spatial resolution if a thick layer of scintillator is used.

These factors can be seen with more particularity in FIG. 2 which shows the blooming of a single pixel imaged using these conventional scintillators. The vertical axis represents intensity of the pixel and the horizontal axis represents position relative to the center of the pixel with respect to light. One skilled in the art will understand that the broader a particular function of light for a pixel appears on this graph, the lower potential resolution on a photosensitive medium, such as film or a CRT, since this will represent a blooming and a potential for cross-talk between individual pixels. Each line represents different prior art systems. Line 20 represents a Lanex fast screen; line 22 represents a non-structured cesium iodide crystal layer of 220 Micron thickness; line 24 represents a structured cesium iodide layer of 220 micron thickness; line 26 represents a Lanex fine screen; and line 28 represents a structured cesium iodide layer of 75 micron thickness.

Often, as is the case with x-rays, the radiation used to create the image has potentially harmful effects on the subject of the examination. Devices with higher DQE reduce the required radiation doses per viewing and allow more frequent viewings for the observation of the growth rate of abnormalities. The density of cesium iodide and sodium iodide crystals is low, thus, prior art scintillators have a low DQE when the scintillator is thin. DQE can be raised by increasing the thickness, but this is done at the expense of spatial resolution.

Conventional methods of fabrication of scintillators, such as vacuum deposition or chemical vapor deposition, have difficulty making films of single crystals of more than a few microns thick. This, in turn, detrimentally affects the light conversion efficiency of the scintillator.

Once the scintillator converts the x-ray image into visible light, there is often still the problem of inadequate light to adequately resolve objects clearly in the image by a detector in the image intensifier tube. The problem is common in various other applications such as endoscopic or laparoscopic imaging, and non-medical imaging such as night-vision photography, for example. Commercially available systems of the aforementioned types generally use as a detector a room temperature charge-coupled device ("CCD") to electronically capture the image-bearing light. Such a CCD has no gain and, therefore, low signal-to-noise ratio, thus requiring intense light illumination. Each pixel in the CCD converts incoming photons into electron-hole pairs. This conversion is made with an efficiency about 30%. Mainly due to the thermal noise of the readout electronics, there is a large noise produced in each pixel even if there is no input light. This noise is typically 100 electrons per pixel for 10 MHz readout frequency. Therefore, in order to have a reasonable signal-to-noise ratio, about 2000 photons per pixel are needed for a standard CCD at room temperature, with a quantum efficiency 30%.

One solution to this problem has been to use a cooled CCD, which has less noise because it is cooled to a low temperature. Even with the cooled CCD though, a large quantity of photons, approximately 400 photons, per pixel are required to have a reasonable signal-to-noise ratio. Cooled CCDs usually have slow read-out speed.

Previously implemented proximity electron-bombarded CCDs achieve some of the desired sensitivity but have other drawbacks, such as short lifetimes, low gain and high noise levels. Moreover, their image size is limited to be the same as the size of the CCD, thus very small for any practical uses like mammogram.

Implementation with Complementary Metal-Oxide Semiconductors (CMOS) sensors would be less promising, as CMOS sensors have much bigger "noise," the industry's term for annoying little dots or scratches on photos, than even usual CCDs, let alone EBCCDs, and thus even worse pictures in sharpness, quality and sensitivity.

In medical imaging, a further diagnostic advantage is gained by three-dimensional reconstruction of images. Such reconstruction followed by reproduction on the screen of the various representations of tissue, such as the breast, density (similar to representation available in computer tomography) has great clinical values, facilitating the diagnostics and reducing the percentage of errors. However, prior art systems have not been able to reproduce exact spatial fixation of the soft flexible tissue, which is too flexible for its fixation with submillimeter accuracy. Therefore, image shadows do not match accurately enough, to allow the reconstruction of the three-dimensional image with the full resolution of the detector.

Accordingly, it is an object of the invention to provide a fluorescence endoscope with reduced noise and improved sensitivity, resolution and speed of image acquisition to allow the probe and the patient to move nominally without smearing out the images taken at different wavelengths with a single photo-detector.

It is another object of this invention to provide a scintillator that resists blooming and pixel cross talk so as to create a high-resolution image at lower radiation doses.

It is still another object of this invention to provide a scintillator with a high DQE without sacrificing spatial resolution.

It is still another object of this invention to provide a scintillator of high resolution that can be used for both displaying an image on an electronic screen and presenting the image to photographic film.

It is still another object of the invention to provide a CCD and a CMOS detector that operates at low levels of light.

It is still another object of the invention to provide an accurate three-dimensional image.

It is a further object of the invention to provide methods in accord with the above apparatus.

These and other objects of the invention will appear with the descriptions and exemplary illustrations provided hereinafter.

SUMMARY OF THE INVENTION

The aforementioned and other objects are achieved by the invention which provides an imaging system for use in low-light environments or environments where low-levels of such radiation is desirable specifically including endoscopy and mammography.

Fluorescent and other visible light endoscopic applications are provided by an endoscopic probe which could have a diameter less than one tenth of a present endoscopic probe diameter or required radiation doses, but a comparable or improved sensitivity according to the use of a magnetically or electro-statically-focussed EBCCD according to the present invention. Moreover, the high sensitivity implies that the speed of image acquisition in selectable wavelength endoscopy is dramatically improved according to the use of a rapidly-switched optical wavelength filter.

Further improvements include image blur removal to provide an endoscope, which may be hand-held and used to detect previously unknown cancers. Alternate embodiments also include a highly sensitive micro-endoscope, which is implemented as an arteriographic probe for clot removal and, in combination with Raman spectroscopy, provides the analysis of arterial plaques.

In the case of radiation that is other than visible light, a radiation converter is used to convert the radiation into visible light. The radiation converter operates in conjunction with a photosensitive medium in an imaging system. The imaging system being such that the radiation is projected upon a structure and variable absorption of the radiation by the structure imprints an image of the structure on the radiation. The radiation converter then converts the radiation, and thus the image into visible light which, is in turn recorded by the photosensitive medium. The radiation converter comprises a scintillator, usually a film of LSO or $CdWO_4$ coated on a light guide, such as a fiber optic window or light guide, to efficiently convert the radiation into visible light.

The scintillator is adapted to convert a predetermined range of wavelengths of radiation into visible light. Generally, the predetermined range of wavelengths will correspond to the range of wavelengths of light known as x-rays, though other wavelengths may also be used.

The scintillator is attached to the light guide, preferably using an adhesive. To achieve the desired properties, the scintillator is then precision machined to a uniform thickness. Upon excitation of the scintillator by the radiation, the scintillator converts the radiation into visible light. The visible light passes into the light-conductive plate, which is in optical communication with the scintillator.

The light guide provides an optical communication path through which the visible light is transported to the photosensitive medium.

The visible light is passed into a signal amplifier employing an electrically or magnetically focussed electron-bombarded charge-couple device (EBCCD) as the photosensitive medium to amplify the signal. The EBCCD records the light electronically and communicates an electronic representation of the image transmitted by the light to electronic circuitry associated with the EBCCD. In this way the image can be portrayed on a standard cathode ray tube ("CRT"), or other type of computer displays, or it can be directly printed onto a photographic media such as photographic film or standard x-ray film.

A further embodiment of the present invention uses the noiseless amplification. of electron-bombardment to enhance the signal or reduce the noise of a CMOS detector. Replacing the CCD detector chip used in an EBCCD tube with a CMOS chip provides an EBCMOS tube with the added advantages of:

1) Image-processing functions can be crammed onto the CMOS sensor chip,
2) Lower cost,
3) Faster readout, and
4) less battery power than CCD sensors.

If a three-dimensional image is desired then an angle associated with the path of the radiation is changed such that a stereo pair of images is created.

If there is object movement in the image then such movement is compensated for by analyzing and synchronizing the images. In further aspects, the invention provides methods in accord with the apparatus described above. The aforementioned and other aspects of the invention are evident in the drawings and in the description that follows.

BRIEF DESCRIPTION OF THE DRAWINGS

The foregoing and other objects of this invention, the various features thereof, as well as the invention itself, may be more fully understood from the following description, when read together with the accompanying drawings in which:

FIG. 3 shows a block diagram of a preferred embodiment of the fluorescence endoscope including a focussing EBCCD having no phosphor light transmitting screen according to one embodiment of the present invention;

FIG. 3A shows a cross-section of the probe according to the embodiment of FIG. 3;

FIG. 9A shows a longitudinal elevation view of the electron trajectories according to the embodiment of FIG. 9;

FIGS. 10A and 10B show longitudinal and axial elevation views of a magnetic focussing element according to one embodiment of the present invention;

FIGS. 11A and 11B show longitudinal and axial elevation views of a magnetic focussing element with greater than unity image-to-detector area ratio according to one embodiment of the present invention;

DETAILED DESCRIPTION

While the present invention retains utility. within a wide variety of electronic imaging devices including mammography and may be embodied in several different forms, it is advantageously employed in connection with endoscopic systems using UV, visible and IR light and x-ray radiation. Though this is the form of one preferred embodiment and will be described as such, this embodiment should be considered illustrative and not restrictive.

Figure 3B:
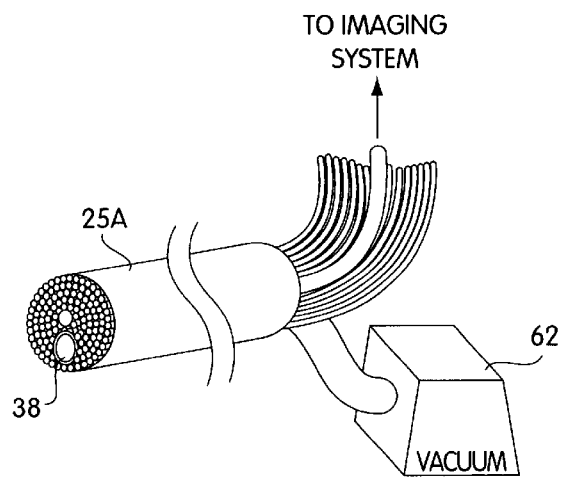
FIG. 3B shows a perspective illustration of an alternate probe according to a further feature of the present invention.

FIG. 3 shows an exemplary fluorescence endoscope, wherein the target tissue 26 is illuminated with a visible light radiation from a source 22, typically comprising a laser (or a filtered xenon or mercury light or white light for the embodiments discussed below), via optics 23 and excitation fibers 24A of probe 25. The target, illuminated with the radiation from the source 22, returns a visible image to the image detector 46 according to the present invention via the collection fibers 24B, optics 2:7, and a tunable color filter 42. In the preferred embodiment, the tunable color filter 42 comprises the liquid crystal tunable filter of Cambridge Research & Instrumentation, Inc., of Boston, Mass., model VS-RGB-GP, or equivalent, the specifications and application information being incorporated by reference. Also included in the endoscope of FIG. 3 is a frame grabber 43, trigger 44 and controller (PC) 45 which operates to store and evaluate the images provided by the image detector 46.

With the magnetic or electric-focussed EBCCD 46, discussed in detail further below, and the liquid crystal tunable filter, the fluorescence endoscope according to the present invention causes the filter 40 to select a green-pass band, and provides a green image of the target tissue 26 to the detector 46, and provides a stored image thereof in the image frame which is copied to the read-out frame in 0.006 seconds. Second, the filter then selects a red-pass band, and provides a red image of the target tissue 26 to the detector 46, and a stored red image is provided in the frame grabber 43 according to trigger 44 and computer 45 within a few milliseconds after the first (green) image is taken and stored. This shortened interval permits accurate images to be made without time for the patient, probe or laser beam to move significantly. Thirdly, the preferred. embodiment calculates (and displays) an image of a the ratio of the red-to-green images. The pair of the green and red images are taken in a total time period of less than 0.006 seconds, compared to prior art systems which typically require at least 0.4 seconds for such image processing. The clusters of high red/green ratio are candidates for cancers. If the probes are moved one pixel (0.012 mm) per interval (0.006 sec.) or 2 mm/sec., the fluorescence endoscope according to one embodiment of the present invention provides rapid screening for cancers.

According to one embodiment of the present invention as illustrated in FIG. 3A, the collection fibers 34B are disposed in a 2-dimension array of fibers with a single excitation fiber, preferably but not necessarily disposed mid way within the collection fibers.

An alternate embodiment according to the present invention, a very small endoscopic system using a white light or infrared light source instead of laser is provided, wherein the probe is introduced into the blood vessel and advanced therein until the desired regions are reached. This embodiment can scan, inspect and analyze tissues (blood vessels, adherent clots, etc.) using not only the reflected light from the surfaces, but also the transmitted light to inspect the structure deep in the tissue with lower radiation damage. Moreover, to prevent clots loosened from the blood vessels from flowing further into the brain, a supplemental lumen (tube) 38 in the probe 25A is connected to a controllable vacuum source 62 in FIG. 3B to evacuate such clots when detected.

A further alternate embodiment according to the present invention generally illustrated by the system of FIG. 3 provides a system for Raman spectroscopy, wherein an appropriate laser 32 light is applied to the target tissue 36, and the emitted light image is provided to the imaging detector 46 via an appropriate wavelength very narrow band filter or grating system (where the collection fibers are disposed in a collinear alignment) in place of the liquid crystal tunable filter 42 to remove the incident radiation and permit the imaging system to measure the wavelength of the target tissue light to a high accuracy. This embodiment can scan, inspect and analyze tissues (blood vessels, adherent clots, etc.) using the emitted light to inspect the chemical content of the material.

Figure 4:
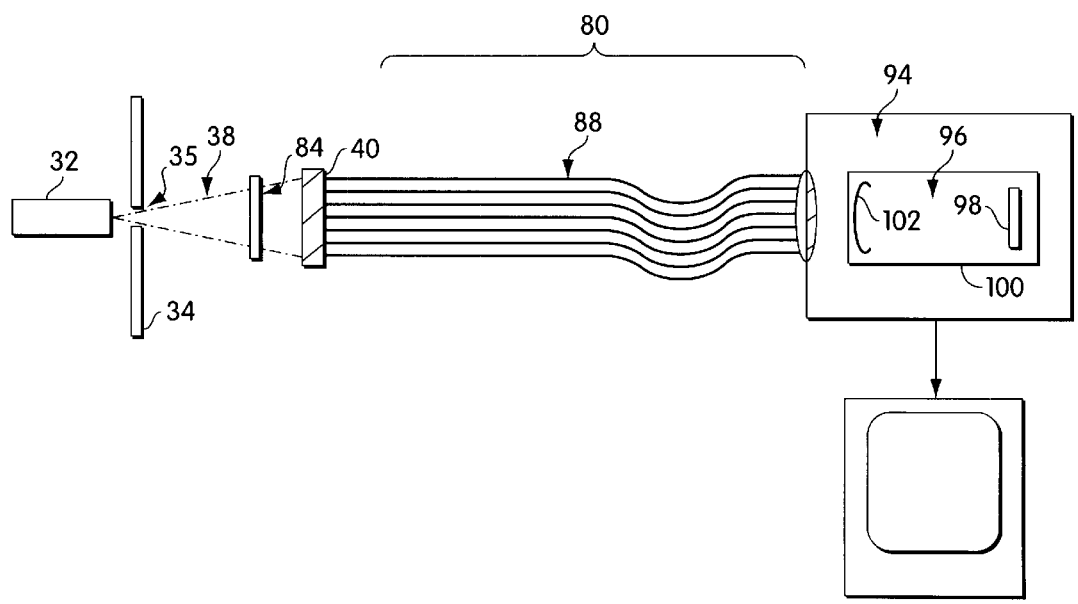
FIG. 4 shows an x-ray endoscope according to one embodiment of the present invention.

Referring now to FIG. 4, an x-ray endoscope 80 is shown having a fiber bundle 82 that is inserted into a patient's body to view an object 84, an organ (e.g. prostate) for example. The endoscope system 80 has a radiation source 32 which projects radiation 38. When actuated, a shutter 34 opens allowing the radiation 38 to pass through an aperture 35 created by opening the shutter 34. The radiation then penetrates into the object being examined, a target 84, e.g. a prostate. The radiation source 32 projects high-energy photons having a predetermined range of wavelengths into the target 84. In the preferred embodiment, the high-energy photons are x-rays having a wavelength in the approximate range from 0.01 to 100 nanometers. The radiation 38 is selectively absorbed by the target 84 tissue thereby imparting an image onto the radiation 38 called a radiation shadow.

The radiation converter 40 converts the radiation 38, and thus the image transmitted thereby, into image-bearing visible light.

The conversion is preferably performed such that the image represented by the image-bearing light is substantially identical to the image transmitted by the radiation 38.

To achieve the aforementioned results, the radiation converter 40 must be fabricated to have a high spatial resolution and a high detective quantum efficiency ("DQE"). Further, a higher DQE results in a endoscopic system 80 that requires less radiation to produce an image, thus reducing health risks to a patient due to exposure to the radiation. Detective quantum efficiency is defined as the square of the ratio of the signal to noise ratio of a real detector to the signal to noise ratio of an ideal, or perfect, detector, ie., $$DQE=[(S/N)_{out}/(S/N)_{in}]^2$$

$$\Lambda[(S/N)_{out}]^2/N$$

for N incoming photons.

In the preferred embodiment the radiation converter 40 has a spatial resolution of approximately 33 microns full width half maximum ("FWHM") of the line spread function and a DQE of approximately eighty (80%) percent for 20 KeV x-rays, a common transmission rate in mammography. FWFM is defined as line width at fifty percent of peak probability. Therefore, there is an approximately 78% probability of being within the region of FWHM. These levels were previously not attainable in the art. The invention attains these levels by fabricating the radiation converter 40 in a novel way.

Figure 5:
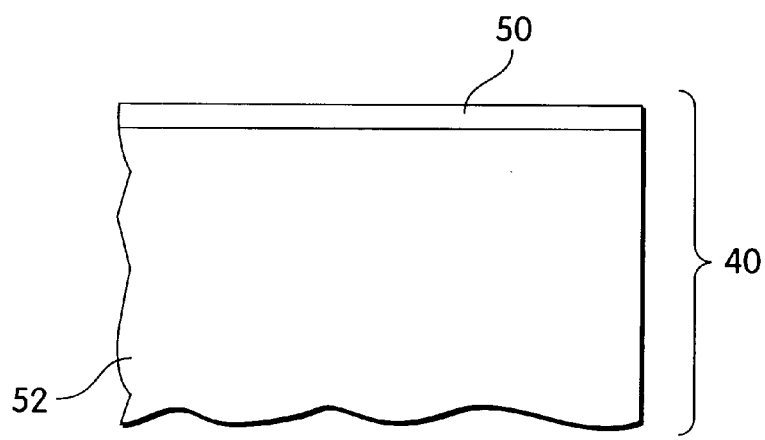
FIG. 5 shows a schematic of the radiation converter of FIG. 4.

With reference to FIG. 5 and continuing reference to FIG. 4, the radiation converter 40 of this embodiment is comprised of a scintillator 50 attached to a fiber optic plate 52. The scintillator 50 is a substance that glows when hit by high-energy particles or radiation. In making the radiation converter 40, the scintillator 50 is glued to a substantially planer fiber optic plate 52 which is comprised of millions of tiny fibers glued together.

The fibers are on the order of 5–10 microns in diameter and act to transport the light to the photocathode 102. Each of the tiny fibers transmits light for one, or a portion of one, pixel in the image. Optical fibers are immune to electromagnetic interference (from lightning, nearby electric motors, and similar sources) and-to cross-talk from adjoining fibers, and thus maintain a sharper image during transmission to the photosensitive medium 98.

In the preferred embodiment, the image-bearing light is then passed into a photocathode e.g. 102 and is imaged onto a photosensitive medium. The photocathode 102 is necessary for use with an FEBCCD which is the photosensitive medium used in the preferred embodiment. However, the photocathode 42 need not be used with a convention CCD. Also, in the preferred embodiment, the photocathode 102 translates light into electron emissions and therefore, the photosensitive medium is photoelectron sensitive as is well known in the art. The image intensifier tube 102 and the photosensitive medium are housed within a light-tight housing 46 such that the only light presented onto the photosensitive medium is the image-bearing light from the radiation converter 40. The photosensitive medium can be any of various devices well known in the art, such as photodetectors.

In the case that the photosensitive medium is a photodetector, an electronic representation of the image transmitted by the image-bearing light is created within the electronic detector and is transmittable digitally to other electronics. For example, electronic representation is digitally transmittable to a computer for immediate viewing. Such viewing can be achieved in real time such that images from the endoscopic systems provided herein are displayed substantially instantaneously. Further, the computer can perform digital signal processing on the image in real time or in an off-line mode where the criteria of the digital signal processing are governed by the physician or an assisting technician. In this way, low contrast details in the endoscopic images can be analyzed by the physician and precise locations of abnormalities can be ascertained for later biopsy should that be needed. On-line digitization allowing for many possibilities of improving the image quality with digital signal processing.

Additionally, since the image is digitized, the image may be viewed on a computer either attached directly to the endoscopic systems or remotely so that the image can be viewed within the same room, across town or across the world using computer communication technology well known in the art.

The scintillator 50 is much heavier than conventional scintillators but with a substantially equivalent light yield and is, therefore, a much more efficient converter of radiation. Further, the scintillator 50 is made thinner relative to other prior art. scintillators while also achieving better spatial resolution and higher DQE. The scintillator 50 is heavier due to a density of at least 6 grams per cubic centimeter. This density increases the ability to precisely machine the scintillator to the desired thickness as well as have a large DQE with a scintillator sufficiently thin to maintain excellent spatial resolution. In the preferred embodiment, the scintillator 50 has a density of 8 g/cm$^3$ and is comprised of a cadmium tungsten oxide (CdWO$_4$) or lutetium oxyorthosilicate (LU$_2$SiO$_5$).

The use of high density scintillators with FEBCCD is novel as the light yields of high-density scintillators are to low to be useful for other types of low sensitivity detectors, such as CCD and silicon photo-diodes, but are useful when combined for high sensitivity FEBCCD detectors which detect a single photo-electron. These choices of materials, in conjunction with a focussing EBCCD detector, increase the DQE and spatial resolution of real time digital imaging devices. One skilled in will realize that numerous other compounds may be substituted for those described above without detriment to the invention. Preferably though, the compound has sufficient density and produces a sufficiently large light yield to convert radiation to visible-or IR light (300 to 900 mm), is radiation resistant, and has an index of refraction not much higher than that of optical fibers.

Once the scintillator 50 is attached, the radiation converter 40 is precision machined to reduce the thickness of the scintillator 50, approximately 50 microns thickness in the preferred embodiment. The thickness of the scintillator 50 is determined in the design stage by balancing the DQE against spatial resolution.

Figure 1:
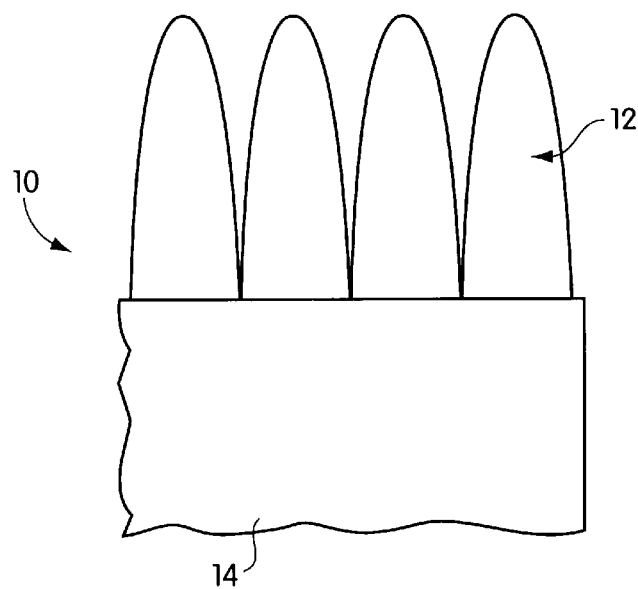
FIG. 1 shows a schematic diagram of a prior art scintillator.
Figure 2:
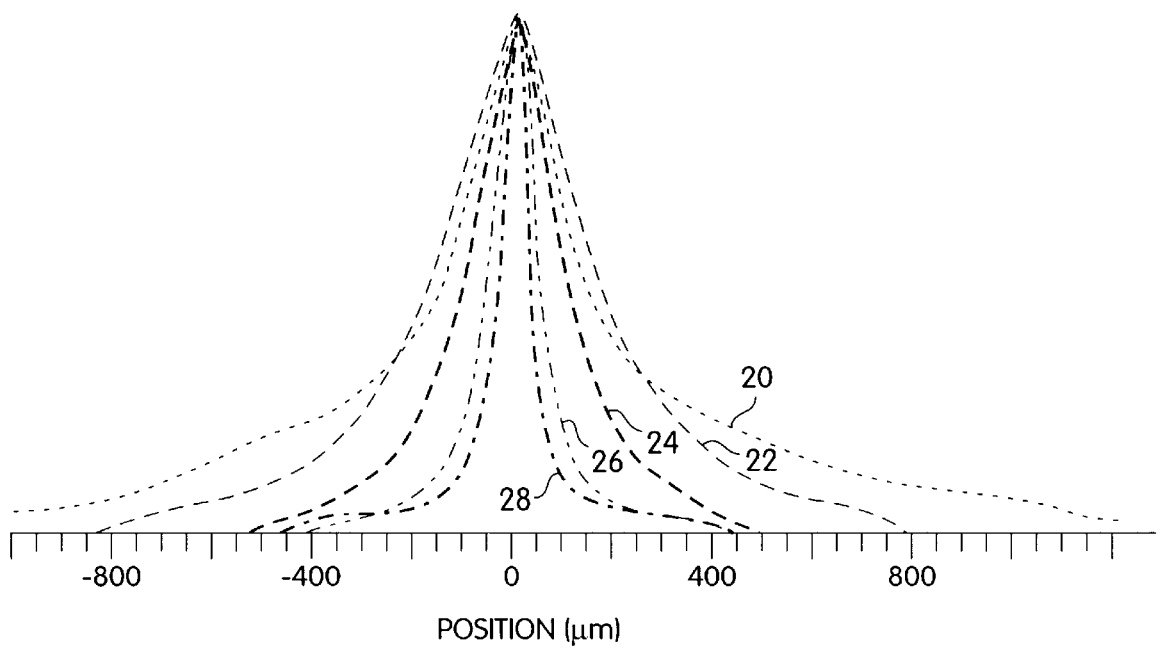
FIG. 2 shows a series of graphs representative of light intensity with respect to position for a single pixel in various prior art scintillators.
Figure 6:
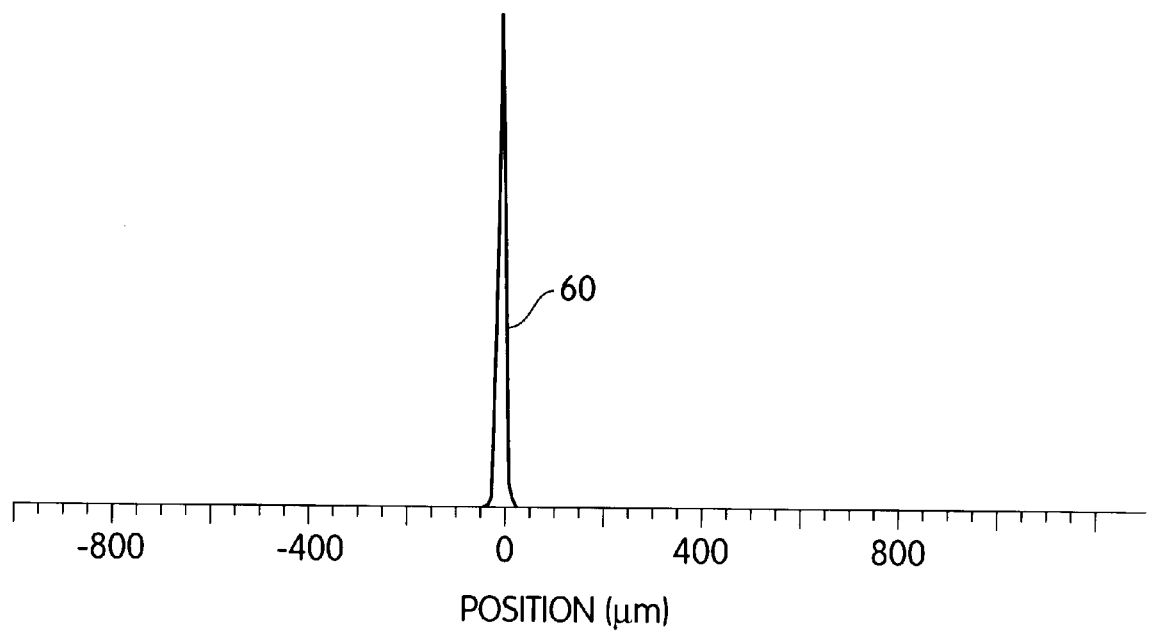
FIG. 6 shows a graph of light intensity versus position for a single pixel generated by the scintillator of the radiation converter of FIG. 5.

FIG. 6 is a graph of position versus intensity for a single pixel using the scintillator of the invention. The graph uses the same axes as that described for FIG. 2 for comparison purposes. It can be seen that the pixel described by the graph 60 has far less cross talk and blurring than those shown in the prior art have.

In alternative embodiments of the invention, the scintillator 50 is adapted to convert other types of radiation. In one embodiment, the scintillator 50 converts ultra-violet light. In this embodiment, the scintillator 50 is a thin, approximately 500 nanometer, layer of material, p-terphenyl or sodium salicylate for example, that phosphoresces when exposed to ultraviolet light. The ultraviolet light is thus converted into visible light, which is guided by the fiber optic plate 52 to the photosensitive medium 98 as previously described. One possible application of this system is ultra-violet imaging of the night sky to find new stars.

Another embodiment of the scintillator 50 converts infrared light. In this embodiment, the scintillator 50 is a thin layer of Gallium Arsenide, which phosphoresces when exposed to infrared light. The infrared is thus converted into visible light, which are converted into electrons and transmitted to the photosensitive medium 44 as previously described. Additionally, the photocathode 42 is changed to a gallium-arsenide photocathode to convert photons into photoelectrons. Applications for this system include use in a night vision cameras or night vision goggles.

Returning to the x-ray endoscopic system 80 of FIG. 4, a set of optical fibers 88 which collects light from the radiation converter 40 within the body and then transmits the light to a camera 94, wherein the light is transmitted into an EBCCD 96 which translates the light into an electronic signal.

Typically when the diameter of a fiber bundle is reduced by a factor of ten as is the case in this embodiment as compared to conventional endoscopes, there is a loss of photons on the order of a factor of approximately 1000 in the intensity of the resultant images. The EBCCD 96 used in the invention compensates for the loss of light by being a factor of approximately 1,000 more sensitive than conventional CCD cameras. Thus for the same quality of image intensities, the endoscope 80 of the invention can be about a factor of ten smaller in diameter (e.g. 1 mm compared to 5–10 mm in the prior art), or a factor of 100 smaller in area.

In comparison, the EBCCD device used in the present invention has a linearity range of 10$^4$ and a resolution about 20 microns FWHM which are focused and accelerated to 3 to 15 KeV by electrostatic field.

Figure 9:
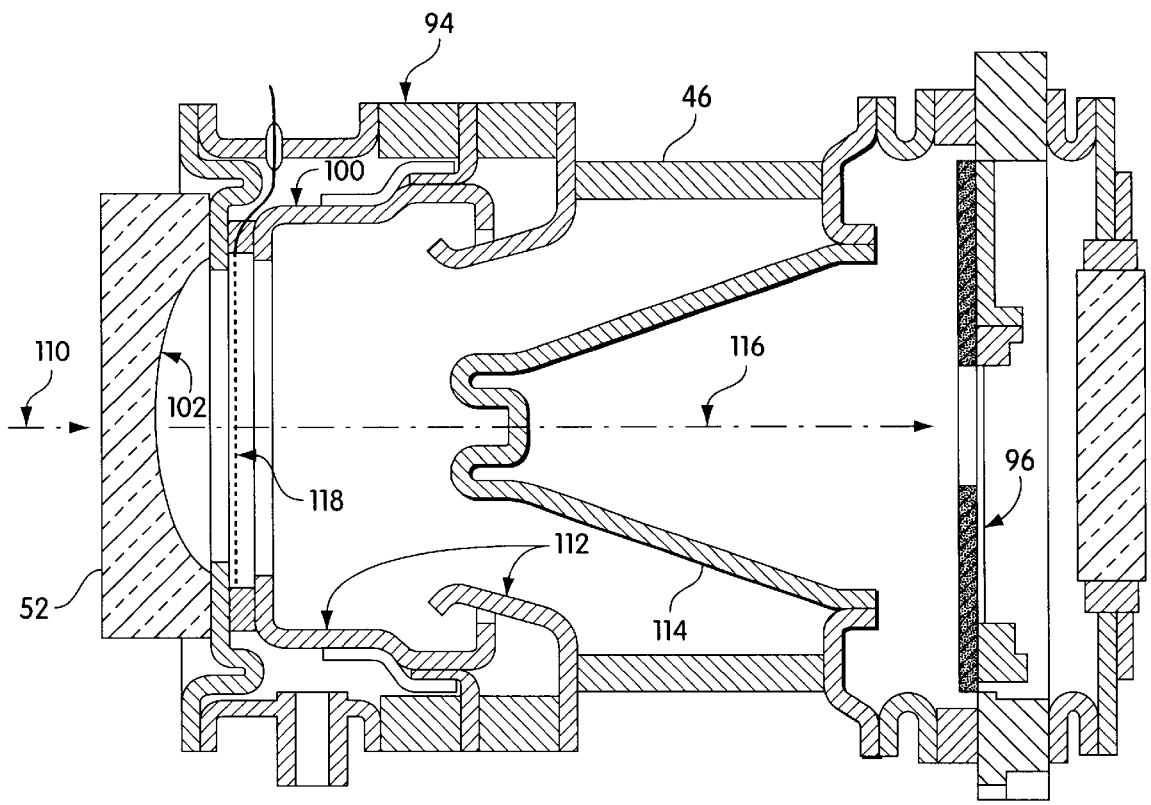
FIG. 9 shows a schematic diagram in partial cross-section of an electron-focussed EBCCD or EBCMOS camera according to one embodiment of the present invention having an electrostatic focussing element.

The EBCCD or EBCMOS 96 uses a photocathode 102 installed in a vacuum tube 100 to convert an optical image of the object 84 into electrons. A detector 98 then receives the electrons from the photocathode 102 to form an electronic image of the object 84. According to the present invention, the detector 98 typically comprises either an Electron Bombardment CCD (EBCCD) or an Electron Bombardment CMOS (EBCMOS) detector, and is referred to for simplicity as an EBCCD 98 hereinafter. The CCD detector may be (but not limited to) an available CCD image detector, and the CMOS detector may comprise (but not be limited to) an available CMOS image detector, such as the Canadian Photonics Labs (Manitoba, Canada) CPL1800C device. The photons transmitted from the second set of fibers 88 are converted by the photocathode 102 of the EBCCD 100 into photoelectrons with a quantum efficiency of approximately 10%. Each photoelectron is accelerated to approximately 3–15 KeV to bombard the detector 98 through an electronic lens system having electrostatic focussing as shown in FIG. 9 and magnetic focussing as shown in FIG. 10. The bombardment results in thousands of secondary electrons being produced in the detector 98. This production of secondary electrons is localized in a very small area thus producing a high gain within the EBCCD 96. This gain allows the EBCCD 96 to detect a single photoelectron. The EBCCD 96, therefore, has an overall single photon efficiency about 10% or more and making the EBCCD 96 several orders of magnitude more sensitive than conventional CCDs or CMOS.

Further, the EBCCD 96 maintains a clear image providing spatial resolution of about 20 micrometers at an exposure level of 10$^{-4}$ lux. By achieving such high resolution at such a low light level, the fiber bundle 88 can be very small thus diminishing the intrusiveness of the endoscope system 80.

Figure 7:
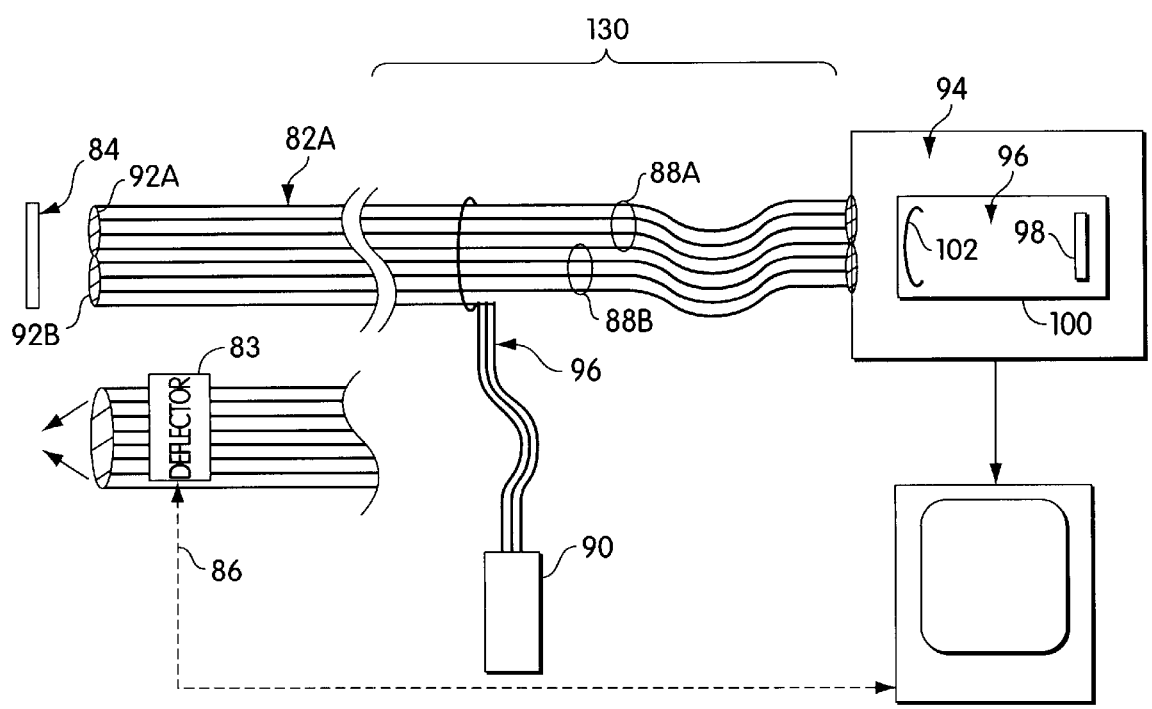
FIG. 7 shows a block diagram of an endoscopic system for generating three-dimensional images according to exemplary embodiments of the present inventions.

A further alternate embodiment according to the present invention is shown in FIG. 7, wherein a 3-dimensional endoscopic system 130 includes a fiber bundle 82B that is inserted into a patient's body to view an object 84, an organ for example. A first set of fibers 86 transmit light from a light source 90 into the body to illuminate the object. The light source 90o is typically a xenon lamp with 200–300 watts of power, or the source 22 of FIG. 3.

A pair of objective lenses 92A and 92B, disposed in front of a corresponding second pair of fibers sets 88A and 88B, collects light reflected from the object 84 within the body and transmits that reflected light to a camera 94A adapted to receive a pair of images but otherwise corresponding to the camera 94 of FIG. 4. In the camera 94A, the light is transmitted to an EBCCD 96 which translates the light into an electronic signal.

An alternate implementation of this embodiment provides a binaural view of the object 84 with an optical deflector 83 which at least two different views of the object 84 to the camera 94A in response to or providing a view position/synchronizing signal 85 to permit proper image processing.

Figure 8:
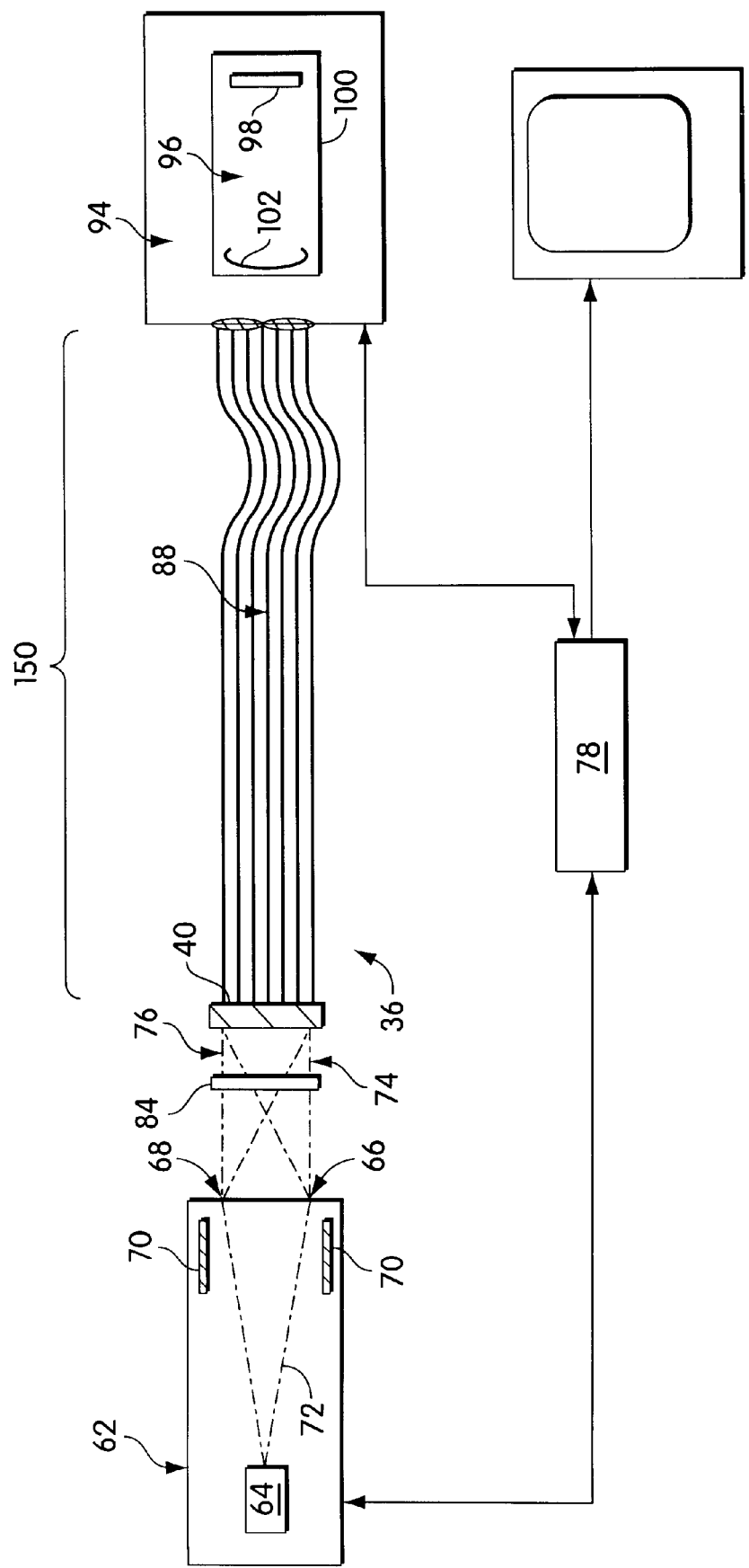
FIG. 8 shows a block diagram of an x-ray endoscopic system for generating three-dimensional x-ray images according to an exemplary embodiment of the present invention.

In another embodiment of an endoscopy system 150 shown in FIG. 8, high-resolution stereo-X-ray photographs and stereo-pairs of three-dimensional ("3-D") images can be generated. Digital imaging has the capability to make 3-D reconstruction of images.

The reconstruction that obtains a substantially matching projection of a particular target 84, such as a soft organ, is accomplished by moving the radiation source 62 electronically without any mechanical alteration of the fixation of the target tissue 84 or the photosensitive medium 98 via the radiation converter 40, fiber optic bundle 88, etc as explained above with regard to FIGS. 4 and 7. An electronic shift is used to shift the radiation source 62 such that the target tissue 84 has virtually no time to change its shape and position, regardless of whether it is firmly fixed. In the preferred embodiment, an image is taken every one millisecond, so every pair of images is not mismatched due to fixation fault.

The electronic shift of the radiation source 62 requires either the use of two or more switchable radiation guns, or, as is provided in the preferred embodiment, a single radiation gun 64 with several targets 66, 68 and a deflection system 70 shifting the radiation beam 72 from first target 66 to second target 68. Deflection is then achieved by applying an external, either electric or magnetic, field to relocate the radiation beam between the targets 66, 68. Generally, the distance between targets 66, 68 is on the order of 1 cm, though one skilled in the art will realize that numerous configurations are possible. In the preferred embodiment, the position of the radiation beam 72 is electro-magnetically shifted from the first target 66 to the second target 68, about 1 cm. within less than three milliseconds in a manner similar to that of a CRT. Such a rapid shift of the radiation beam 72 requires the radiation source 62 that has at least two targets 66, 68 and a deflection system 70.

As previously stated, the radiation source 62 may have several switchable cathodes or a pair of X,Y deflectors 70. However, instead of using two sine wave oscillators with a 90 degree phase shift relative to each other which makes the electron beam move in a circle, a step-pieced approximation is used. Assuming the step duration of T seconds, the electron beam will stay in a position X(i), Y(i) during T and during the next step—in a position X(i+1), Y(i+1). A step-pieced function is prepared by a special programmable function generator and then is amplified by a power driver up to a few hundred volts as in oscilloscopes, as is well known in the art. There are an arbitrary number of anodes. If step-pieced function is synchronized with the detector, any slice can be obtained.

In either of the previously described radiation source configurations, two radiation shadows 74, 76 are generated. The first radiation shadow is projected onto the radiation converter 40 and is converted into visible light. The visible light then impinges upon a detector 77 which generates an electronic representation of the image in the visible light. One skilled in the art will realize that in the case that the detector is an FEBCCD, electron-hole pairs would impinge upon the-detector 77 and a photocathode (not shown) would convert the visible light into the electron-hole pairs. The electronic representation is then transferable to a computer 78 which is adapted to display the image. Likewise, the second radiation shadow is converted and transmitted to the computer 78. Thus, the two radiation shadows 74, 76 become a stereo-pair, each presenting a different angle of the image. The stereo pair is then manually adjusted to the distance between human eyes to form a 3-D image. Human eyes are able to recognize the nature of objects and to distinguish more details on a stereo image better than on a flat one. In particular, the numerous shadows of fibrous tissues in mammary glands impede the observation of low-contrast formations in flat images but not necessarily in stereo images. Moreover, if a physician viewing the 3-D image notices anything clinically interesting in the image, the stereo-pair can be further processed by a computer 78 and a three-dimensional distribution of the organ density can be reconstructed.

Further, as the number of exposures from differing viewpoints increase, a physician can see structures within the organ to from different sides. Since the generation of the screen image on the computer 78 can be-done during a fraction of a second, the choice of the next view-point can be done interactively, depending on what was seen already. Moreover, these new angles provide additional data such that the computer 78 can more accurately model the structures creating rotatable images and providing the physician with numerous viewing options.

The radiation source 62 for 3-D imaging is designed to have two notable distinctions from a typical radiation source. First, conventional radiation sources are usually made to produce substantially parallel (weakly divergent) rays, so the radiation source is placed far from the object and is collimated in both position and angular acceptances. In contrast, the radiation source 62 of the invention provides divergent rays and, therefore, can be close to the object and needs no collimation in angular acceptance. Hence, the radiation source 62 needs less power and smaller security shielding, and the radiating spot produced by the radiation beam 72 is smaller which improves image resolution. Moreover, the radiation source using divergent radiation beams is easier to make than a radiation source requiring tightly collimated beams.

Second, to generate mathematically tomographic slices and/or stereo-views from several photos taken in collimated beams as is done in the prior art, a very difficult full-scale tomographic reconstruction is needed. However, if divergent beams are used, two images captured for two source positions form a stereo pair without any mathematical processing. In most cases, the stereo pair may be used instead of tomographic slices. In such cases, computer processing may be needed only to change the scale, to subtract background, to improve contrast, or to perform other image processing. Interactively is also enabled in this way. For example, if a small calcification is seen and marked by a computer pointing device, the computer locates exact coordinates of calcification grain in space.

In another embodiment, the radiation beam 72 is continuously deflected producing generating dozens of different image shadows registered by the detector 44. This produces images that can be interactively "focused" by a physician to various levels, or depths, within the target tissue 84. For example, Let N represent the number of image shadows registered by the detector where each image shadow is obtained from a different position of the radiation beam 72. Assume that the object being viewed contains a small abnormality, such as a small grain-like calcification. The position of the shadow generated by the abnormality on each image shadow will be different. The relative shift of the shadow positions on different image shadows is proportional to the distance from the abnormality to the detector 77 and can be calculated from the known positions of the radiation gun 64 and an assumed distance, L, of the abnormality from the detector. To calculate, a total shadow density, the image shadows are shifted such that the image shadow of the abnormality occupies the same place on all the images. The signals (shadow densities) from all N images are then summed. The shadow density from this abnormality and the signals from all other details of the object that are situated at the same distance L from the detector 77 as the given abnormality will sum and become N times bigger. However, the shadows from the details that are closer to the detector or are farther from the detector 77 are displaced on different images and the summation of the signals will not increase these details. Therefore, on the summed image, these details will appear in N copies, each copy being N times less intense than the signals from details situated at distance L. If N is in the range of 20–40 or more, the images of the details of the object that are not at the distance L are practically invisible and make a blurred background. The summed picture however, is clear. The overall image is then analogous to the image visible in a short-focus microscope: only the details lying in the focal plane are sharp and visible, the details that are a bit closer or farther away are blurred. Thus, having a multiple images from slightly shifted point sources enables reconstruction of any slice of the object parallel to the detector window.

In usual tomographs, reconstruction requires substantial computing and is time intensive. In the invention as described, reconstruction is reduced to very simple mathematical operations: shifts of the images as a whole and summation of signals. The reconstruction can then be performed in real time and interactively, where selectively changing a position of the focal plane of the slice by pressing keys on the keyboard or moving the mouse.

Additionally, since this system differentiates foreground from background, the background can easily be subtracted from the image or a new background can be inserted to enhance viewing, a coordinate grid for example. In fabricating the radiation source of the preferred embodiment, the size of the spot on the target 66, 68 inside the radiation source 62 where the fast electrons are stopped and the gammas are produced is preferably less than 50 microns. Otherwise, the image on the detector 77 will be smeared. The target 66, 68 should be much larger than the source beam 72, preferably 2 cm or more.

As previously mentioned, the photosensitive medium can be an electronic detector. In the preferred embodiment, the electronic detector is optimized for low-light applications, thus requiring less radiation to form an image. Such a detector is known in the art as an focussing electron bombarded ("FEBCCD"). A FEBCCD has a very fine pixel size with excellent spatial resolution as well as a high signal-to-noise ratio at very low light intensities.

Focussing Electron Bombarded Charge-Coupled Device ("FEBCCD") are many orders of magnitude more sensitive than the CCDs currently used in the art. They have particular application in medical systems in which there is difficulty illuminating an object to be imaged. Examples of such systems are endoscopy and laparoscopy. Though these will be described as a preferred embodiment, this application should be considered illustrative and not restrictive.

Use of thinner endoscopes, e.g., about 1 mm diameter, have an obvious advantage of requiring smaller opening in a-patient's body and thus is less painful for the patient during the operation and accelerates healing. conventional endoscopes are 5 or 10 mm though due to high light requirements of conventional CCDs.

Referring now to FIG. 9, a preferred embodiment of the camera 94 is shown. The camera 94 is shown with the optional radiation 110 entering the radiation converter 40 of FIG. 5. As previously described, the radiation converter 40 comprises a scintillator 50 which converts the radiation 110 into visible light. The visible light is then transmitted through the fiber optic plate 52 (directly or through optical fibers) into the light-tight housing 46.

Coated on an interior surface of the fiber optic plate 52 is photocathode 102, which converts the visible light to electrons 116. The electrons 116 are then accelerated by an electric field generated by electrodes 112 and anode 114. The accelerated electrons 116 then impinge upon the EBCCD 96 creating secondary electrons thus amplifying the image conveyed by the radiation 110 or by directly applied visible light. The EBCCD 96 is a megapixel EBCCD 96 with a gain of approximately G=4000 at a tube voltage of 15 keV. The EBCCD 96 has a spatial resolution of approximately 20 $\mu$m at an exposure level of $10^{-4}$ lux. Further, the EBCCD 96 has a comparatively better amplitude spectrum, due to lower gain fluctuation and lifetime of more than 2000 hours at illumination of $10^{-2}$ lux while maintaining a stable gain over the lifetime of the camera 94.

The electrodes 112 are also used to create an electric field to dynamically select demagnification of the detector so as to govern an area of an object to be imaged. In the preferred embodiment, the demagnification can be up to 5.

Thus, by adjusting the electric field, demagnification of the detector is achieved that allow a 1.3×1.3 cm$^2$ detector-to image a 6.5×6.5 cm$^2$ object at present and a 4×5 cm$^2$ detector 20×25 cm$^2$ in the near future.

Exemplary electron trajectories 104 are shown in FIG. 9A for the embodiment 94 of FIG. 9, wherein electrons from cathode 102 follow the electric field lines to pass through a narrow focal point before they hit the CCD 98 in curved trajectories. Most of the positive ions produced when these electrons hit the CCD back scatter to be absorbed by the electrodes surrounding the tiny focal point and thus do no damage or reduce performance.

Magnetic focussing may also be provided according to the present invention as illustrated in FIGS. 10A, 10B, 11A and 11B, wherein exemplary electron trajectories for unity and greater than unity, (e.g. about three as shown) of image/detector size ratios are provided in FIGS. 10A, 10B and 11A, 11B, respectively. A uniform magnetic field is produced by a uniformly wound, constant radius coil 106A to deliver electrons produced by the cathode 102 onto the detector CCD 98 of about the same dimensions as the image impressed on the cathode 102. The magnetic field is parallel to the line joining the centers of the cathode 102 and the CD 98. Each electron from the cathode 102 follows a helix trajectory inside the magnetic field to hit the CCD 98.

Positive ions produced when these electrons hit the CCD 98 back scatter in helical trajectories with a much bigger radius because of their much bigger (>1800 times) masses to get absorbed by the surrounding electrodes, and do not diminish the performance and do no damage. In general, the apparatus according to the present invention which applies the magnetic field may also be generally applied to eliminate positive ion feedback when electrons hit the CCD. The radius of curvature, R, of a charged particle with mass m and charge q in a magnetic field of strength B, $$R = (2\,mB)^{1/2}/(q*B)$$

or simply, R is proportional to the square root of the particle mass, m. Since R of a positive ion is at least 1800 times bigger than that of an electron, the positive ion is likely to hit the wall of the magnet or container, or otherwise diverge from the path of the electron, and get lost without returning to the electron source, e.g. the photocathode or other source.

An image larger than the detector CCD 98 may be provided by a magnetic field tapered toward the CCD 98 as provided by a uniformly wound coil 106 having diminishing radius as illustrated in FIG. 11A to produce the electron trajectory shown in FIG. 11B. Alternate electron trajectories, e.g. 104, etc., and alternate means (not shown) may be used to produce the desired magnetic field contour, e.g. non-uniform winding, magnetic shunts, permanent magnets, and so forth. Moreover, with either the electrostatic or the magnetically focussed embodiment, an image smaller than the detector size may be provided by correspondingly generated electron trajectories according to the present invention.

The EBCCD 96 of the preferred embodiment has 1024× 1024 pixels with pixel size 13.1×13.1 $\mu m^2$ and a sensitive area of 13.4×13.4 $mm^2$, having a-demagnification of up to 5. The EBCCD 96 is manufactured in three phase, i.e., having three electrodes per pixel. Three levels of poly-silicon gate technology using two-levels of gate dielectric ($SiO_2+Si_3N_4$) layer are also used. The EBCCD 96 has an n-type buried-channel structure and the p-silicon has a resistivity of approximately 4–20 Ohms/cm.

The imaging part of the detector 98 consists of an active area divided into two 512 row×1024 column regions which can be shifted up and down independently towards to appropriate output registers. Independent control over the parallel clocking of each of these two areas is provided such that the charge in different areas can be shifted in opposite directions. The output amplifiers are buried-channel MOSFETs connected to floating diffusion nodes where the signal charge is off-loaded.

The EBCCD 96 incorporates Multi-Pinned Phase (MPP) technology to significantly reduce the dark current. The EBCCD 96 is chemically etched in an isotropic silicon etching solution in a rotating disc system in order to make detection efficiency uniform over the entire detector. Preferably, hydro-dynamical rotation is used to obtain thinned EBCcD substrates with thickness to 8 micrometers and non-uniformity less than 10% over the full image area. To obtain a high gain and to reduce recombination, a stable electric field not less than 5 kV/cm is created near the backside surface of the thinned detector 98.

After the thinning procedure, a shallow p+ layer is formed by ion implantation using an annealing technique and surface chemical treatment. Low temperature annealing is used in the preferred method due to its capability to create good image uniformity and low dark current.

A stable "dead layer" having a depth of less than 1000 Å is then created by properly choosing an ion implantation dose and energy which operate with the high values of the internal electric field from p+–p high-low junctions and with the low efficient surface recombination rate of the p+–surface.

The combination of all these technologies result in a stable and uniform detector for electrons above a few KeVs.

After these procedures the detector 98 is mounted into a metal-ceramic housing (not shown) and electrical connections are formed.

The vacuum tube 100 is then mounted around the metal housing. The vacuum tube 100 has a magnification selectably changeable from 0.5 to 5. A photocathode 102 is deposited on the input fiber optic window, which is the terminus of the second set of fibers 88. Preferably, the average quantum efficiency of the photocathode 102 is 10% at 500 nm or better. In the preferred embodiment, The maximum voltage on the photocathode 102 is 20 kV.

The EBCCD 96 is installed with the use of a vacuum flange by laser welding. The vacuum tube 100 is then annealed at temperature less than 320° C. Afterwards the photocathode 102 is made on the fiber optic plate 52.

Figure 12:
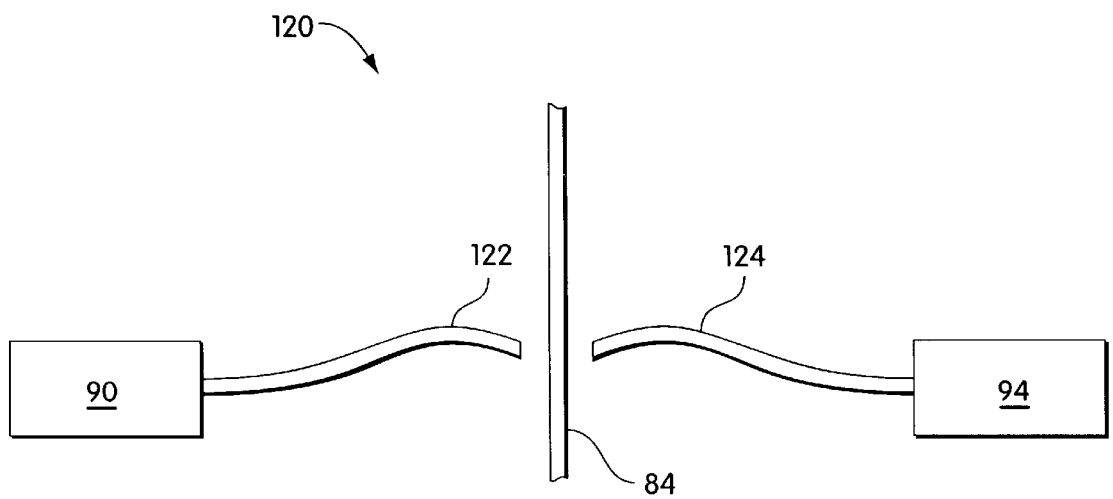
FIG. 12 shows a block diagram of a transmission endoscope utilizing the camera of FIG. 9 according to one embodiment of the present invention.

Another application of the invention is for use as a transmission endoscope 120 as shown in FIG. 12. Since an EBCCD is extremely sensitive to light, a light source 90 can be placed one a first side of an object 84 and the camera 94 on a second side of the object 84. opposed to the first side. The light from the light source 90 can directly illuminate the object 84 or can be transmitted to the object 84 by transmission fibers 122, depending upon where the object 84 is located. Light passing through the object 84 is gathered by the receiving fibers 124:provides as and endoscope, and transmitted to the camera 94. As previously described, the image is then displayed or recorded.

In the aforementioned medical systems, object motion is corrected by imaging at rates of speed greater than the rate of object motion. Further, color imaging is generally not used and, therefore, the need to register individual pixels is not of consequence. However in other applications of the invention such as low-light photography, fast-moving objects and color registration of a moving object becomes a significant problem.

To accomplish color registration of a moving object thereby removing any blur instilled by the motion, the invention uses either three photo-detector to receive the pictures of each color component at the same time or one photodetector with several rotating color filters to receive the information of the color components in several subsequent time frames. The latter method is commonly known in the art as time-delay integration. The time frames are separated by a. time interval of approximately 0.01 second between consecutive frames. The problem can be expressed algebraically as follows. Let $R_{ph}$ $G_{ph}$ $B_{Ph}$ be the average number of photons per pixel passing through the red, green, and blue filter per pixel respectively. The average number of photo-electrons for each of the red, green and blue components is:

$$N_R = R_{ph} \cdot QE(\pi) \cdot t, \quad N_G = G_{ph} \cdot QE(\pi) \cdot t, \quad N_B = P_{ph} \cdot QE(\pi) \cdot t,$$

where $QE(\pi)$ is the quantum efficiency of photo-sensor, and t is the color filter transmission. The number of photo-electrons in different pixels fluctuates independently according to the Poisson statistics. Noise due to detector and electronics is added in each pixel with its fluctuation assumed to be a Gaussian. If, however, the object is moving too fast relative to the exposure time of the camera, then the standard deviation of the fluctuation increase dramatically resulting in a blurred image.

In the case of using three photo-sensors, all three color components, red, green and blue, are available at the same time. A single beam of image-bearing light enters a camera and is split by diachronic mirrors to transmit color components of the light toward individual photo-sensors. The image capture time is primarily dependent upon capture time of the photo-sensors.

A single photo-sensor with four rotating color filters may be used. When very limited amount light is available and/or when only one photo-sensor is available, due to the compactness of night cameras for example, time-delay integration is a preferred method of taking color images. In this case, the main task of the image reconstruction is to combine images captured at different moments in time and with different color filters into a single correctly colored image. This is known in the art as color reqistration. To accomplish this, it is necessary to compensate the motion of the object between image captures to reduce the smearing of the images due to the motion during a finite, approximately 10 msec, exposure time, and to suppress the Poisson fluctuations of the photon numbers.

The procedure of reconstruction is preferably also resistant to bad conditions, when some of the images are captured with insufficient light or other obstacles intercede, such as a bird flies into the view for example. Under such circumstances, the colors are slightly distorted, but the outlines of the details are still correctly reproduced. The motion of a slow-moving object is compensated by scaling, interpolating and aligning the corresponding pixels of the four different pictures.

For a brightness of color i of an image at a certain point in an object is b, prior to influence by the color filters, the average number of photo-electrons at the corresponding pixel after the color filters is $$A_j = \Sigma_i t_{ji} \cdot QE_i \cdot b_i \cdot T \cdot S,$$

where S is the area of the pixel and T is the exposition time. In matrix form, $A_j = C \times B$, where $C_{ji} = t_{ji} \cdot QE_i$ are attenuation coefficients, and $B_j = b_i \cdot T \cdot S$ are the number of incoming photons. In the preferred embodiment, the color wheel has two clear filters, or no filter, in two separate filter positions. Images captured through these filters are referred to as W images. The two other filter positions are red, R, and green, G, filters. Blue is determined by subtracting the R and G images from a W image.

Two identical W images may be added together with $A_o$ becoming the total number of photoelectrons in two shots and with the coefficients $C_{i0}$ doubled. Then matrix C become 3×3 and, thus, the numbers of incoming photons are calculated by means of its inverse $C^{-1}$ as $$B = C^{-1} \cdot A.$$

Replacing the unknown averages $A_j$ by the numbers $a_j$ of actually produced and registered photo electrons, we obtain for the estimate $$B = C^{-1} \cdot a.$$

Since numbers-have the Poisson distribution with the dispersions Aj, the estimate B has the correct mean value and the dispersion $$D(B_i) = \Sigma_i (C^{-1})_{ij}^2 \cdot A_j.$$

The lowest image on all figures is the result of color smoothing. The color smoothing is a complicated task since simple color averaging over a. number of nearby pixels would smear the borderlines of regions of different colors and intensities and seriously degrade the resolution of the image, which is not acceptable. Before any averaging, statistical tests are made to check, whether, within the statistical errors, the colors of neighboring pixels differ significantly or not. After a number of repeated averaging, the true borderlines survive, while inside each region the color becomes smoothly changing or uniform.

When an object is moving very quickly though, the blurring of the image can be too excessive to use the aforementioned brightness smoothing. One reason for this is that the borderlines may be indeterminable. If, for example, the object is a license plate of a car traveling at 36 km/hour of transversal speed in dimly light conditions. Assuming a size of one pixel in the camera, approximately 0.02 mm, corresponds to 1 mm in the license plate and the exposure time of the camera is 0.01 seconds. The motion of the car produces a smearing of about 100 pixels in every one of the pictures taken.

Compensation of the shift of the image of the moving object is performed in two steps. First, the amplitudes of several of the lowest Fourier harmonics of the two W images are calculated. From these amplitudes, a coordinate transformation mapping one of the W images into the other is performed. The. corresponding transformations for R and G images can be computed by interpolation. However, after these transformations, most of the pixels of one image will lie somewhere between the pixels of the other image. The second step must then establish the pixel-to-pixel correspondence.

The second step is performed by computing interpolated pixel values before or after the previously described brightness smoothing over the original images. The blurring of the images caused by the motion of the object during the exposition time must first be suppressed though. If the fluctuations were absent, the blurring could be eliminated with arbitrary accuracy by means of a commonly used corresponding inverse integral transformation. However, this integral transformation increases fluctuations. Thus, when the blurring is partly suppressed, the resolution improves; and when the blurring is suppressed too much, the fluctuations increase and the resolution becomes worse.

The choice of the optimal degree of blur suppression and of the actual transformation function must comply with statistical criteria and may be different in differently illuminated parts of the image. Averaging removes some blur, but does so incompletely. The usual inverse integral transformation, disregarding the statistical fluctuations of the image, gives rather poor images, over-shadowed. by heavy random background.

The blur removal method of the invention based on statistical methods makes better use of the information contained in the blurred image and gives much clearer pictures.

Figure 13A:
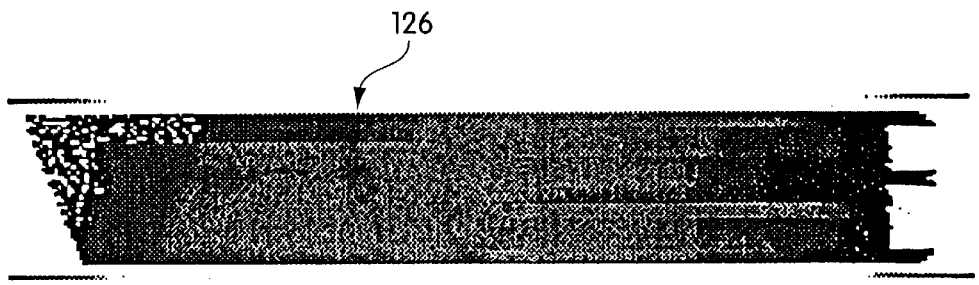
FIGS. 13A and 13B show images before and after image correction as per the invention.
Figure 13B:
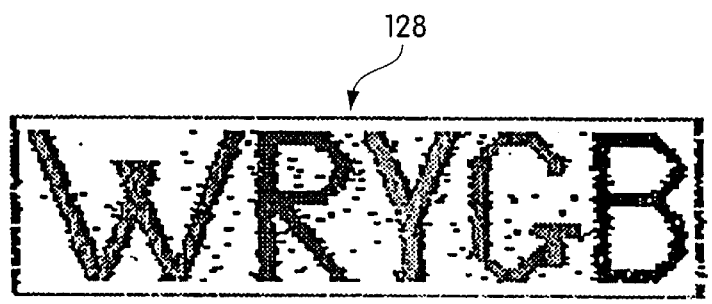

The typical result of blur removal by this method is illustrated by FIGS. 13A and 13B. As shown in FIG. 13A, original image 126 is overexposed (about 200 photo-electrons/pixel/color) and blurred over 100 pixel (Gaussian width) so R=20 photo-electrons /pixel/color. This blurring over 100 pixels is inside each of the W, R. G images. No letters except the left most "W" is remotely recognizable.

As shown in FIG. 13B post-blur removal image 128 has more fluctuations than the original image 126, containing some random background, but is well readable. A similar blur removal effect is achieved for underexposure.

The image reconstruction method includes the analysis of the images to find the optimal parameters of motion compensation, of blur removal, and of color smoothing.

The method of blur removal is based upon the maximum likelihood method and fully exploits a priori non-negativeness of the light intensities. The solution of corresponding equations is done by fast recursive procedures starting from edges of the original image 126. For each pixel in a frame, two statistical estimates are obtained and balanced. The white frame having better statistical accuracy than the color frames is used as a mask for the red and green frames when the post-blur removal image 128 is reconstructed.

The method achieves a resolution of 40 to 60 line pairs at 15% MTF and a gain of approximately 5000, and thus a signal-to-noise ratio of 2 at $4 \times 10^{-5}$ lux, by integrating images over time, i.e. after matching regions with similar shape, color and intensity within certain well defined boundaries in pictures taken at adjacent time.

To reconstruct a colored image such as the original image 126, at least three colors are needed: red, green and blue (R,G,B, respectively), for example.

Light reflected from the original image 126 passes through three filters corresponding to the three colors. The average number of photons that pass through the red, green, blue filter per pixel is then $R_{ph}$, $G_{ph}$, $B_{Ph}$, respectively. The average number of electron-hole pairs for red, green and blue components will be equal:

$$N_R = R_{Ph} \cdot QE(\pi) \cdot T, \ N_G = G_{Ph} \cdot QE(\pi) \cdot T, \ N_B = B_{Pb} \cdot QE(\pi) \cdot T,$$

where $QE(\pi)$ is quantum efficiency of photosensor, T is color filter transmission. Monte-Carlo simulations have been performed for each component of light, i.e., RGB. The number of electron-hole pairs (e–h) in the detector fluctuates according to the Poisson statistics, in different pixels e-h pairs fluctuates independently. Four filters were chosen: W, R, G and W. Two W filters allow reconstructing a moving object more efficiently. The W filters are clear, or white.

The reconstruction of colored image takes into consideration the transparency of the color filters and the different sensitivity of a detector to red, green and blue (R,G,B, respectively) colors. Let index i=0,1,2 correspond to RGB colors, j=0,1,2,3 to 4 consecutively captured images, $t_{ij}$ be the transparency of the filters to photons of color i at shot j, and $q_i$ be the quantum efficiencies of EBCCD to RGB photons. Also, assume that the motion of the object is known. That is, using standard edge detection or other object location techniques, the correspondence of a pixel in one image to a pixel in a subsequent image has been displaced by a known amount.

If the brightness of color i of an optically generated image of the object prior to the color filters is $b_i$, the average number of photoelectrons at the corresponding pixel after the color filters is $$A_j = \Sigma t_{ij} \cdot q_i b_i \cdot T \cdot S,$$

where S is the area of the pixel and T is the exposition time. In matrix form A=C×B, where $C_{ij}=t_{ij} \cdot q_i$ are attenuation coefficients, and $B_i=b_i \cdot T \cdot S$ are the numbers of incoming photons. Two identical W shots may be simply added together with $A_o$ becoming the total number of e in two shots and with the coefficients $C_{i0}$ doubled). Then matrix C becomes 3×3, and the numbers of incoming photons are calculated by means of its inverse $C^{-1}$ as $B=C^{-1} \times A$.

Replacing the unknown averages $A_j$ by the numbers $a_j$ of actually produced and registered electrons, we obtain for B the estimate $$B = C^{-1} \times a$$

Since numbers $a_j$ have the Poisson distribution with the dispersions $A_j$ the estimate B has the correct mean value and the dispersion.

$$D(B_j) = \Sigma (C^{-1})_{ij}^2 \cdot A_j.$$

A test of color reconstruction used an EBCCD having a uniform QE $q_i$=q (EBCCD has q about 0.1), and a transparency of R,G filters set to ½ resulting in matrix C/q and its inverse as $$c/q = \begin{matrix} & R & G & B & \\ & 1 & 1 & 1 & W \\ & 0.5 & 0 & 0 & R \\ & 0 & 0.5 & 0 & G \end{matrix} \qquad q \times C^{-1} = \begin{matrix} & W & R & G & \\ & 0 & 2 & 0 & R \\ & 0 & 0 & 2 & G \\ & 1 & -2 & -2 & B \end{matrix}$$

The letters WRYGB in FIGS. 13A and 13B had colors (1, 1, 1), (1,0,0), (1, 1,0), (0, 1,0), (0,0, 1) corresponding-to white, red, yellow, green and blue, respectively, and their horizontal and vertical lines were 5 pixels wide. Each pixel of letter W got an average 3 photoelectrons at W shot, and ½ of an electron at R and G shots. The images were taken at approximately $0.5 \times 10^{-4}$ lux.

The compensation of the shift of the image of the moving object can be done in two stages. First, the amplitudes of several of the lowest Fourier harmonics of two W shots are calculated. From these amplitudes, the coordinate transformation mapping one shot into another, can be found and the corresponding transformations for R and G shots can be computed by interpolation. However, after these transformations, most of the pixels of one shot will lie somewhere between the pixels of the other shot. The second stage should establish the pixel-to-pixel correspondence by computing interpolated pixel values before or after the brightness smoothing over the original shots.

The quality of the un-smeared image depends mostly on the ratio R exposition/smearing and, to some extent, on the total width of the image and on the color of the background. The black background contributes less fluctuations into the smeared image and is the best for the unsmearing. If the smearing is measured in pixel widths and object is similar to that shown in the example, the ratio R>30 e/pix/col/pixels allows the complete unsmearing up to I pixel. For smaller R, the complete unsmearing is either not reasonable, or (for R<3 e/pix/col/pixel) totally fails due to strong fluctuations, but partial unsmearing to several pixel widths is still possible and may be very useful.

Partial unsmearing may be done by combination of the local averaging of the smeared image over a number of adjacent pixels and the unsmearing. Averaging reduces fluctuations and makes them statistically strongly correlated, what makes unsmearing possible, but blurs somewhat the unsmeared image, so it looks not fully unsmeared. The usual inverse integral transformation, disregarding the statistical fluctuations of the image, gives rather poor images covered by heavy random background. A novel unsmearing procedure based on statistical methods makes better use of the information contained in the smeared image and gives more clear pictures. The original image is overexposed (about 2000 e/pix/col) and smeared over 100 pixel widths so R=20 e/pix/col/pixel. No letters except the left most portion W can be guessed. The unsmeared image is more fluctuating than the original image and contains some random background, but is well readable.

The invention may be embodied in other specific forms without departing from the spirit or essential characteristics thereof; including modifications and substitutions as may be made by one of ordinary skill in the art. The present embodiments are, therefore, to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. An imaging system, comprising,
a radiation source having a first wavelength emission;
a first conduit providing a path for radiation between said radiation source and a selected imaging object;
an electromagnetic focussing imaging detector providing an output signal in response to an applied optical image, wherein said magnetically focussed image detector comprises:
   a photocathode disposed to receive photons and provide electrons corresponding to the intensity of the received photons,
   one of a CCD and a CMOS detector disposed a selected distance from said photocathode to receive said electrons,
   means for urging said electrons toward said one of a CCD and a CMOS detector from said photocathode, and
   a magnetic field source disposed to provide a magnetic field along said selected distance, wherein said electrons are caused to move in a helical path toward said one of a CCD and a CMOS detector of selected radius change; and
a second conduit for applying said optical image to said focussing imaging detector from said selected imaging object.

2. The imaging system of claim 1, wherein said radiation source comprises a light source.

3. The imaging system of claim 2, wherein said light source comprises one of a white light, an ultra violet light, a selectively filtered mercury light, selectively filtered xenon light, a near infrared light and selected wavelength laser light source.

4. The imaging system of claim 3, wherein said light source provides one of a 310–430 nm wavelength visible and a near IR (about 700 nm) light emission.

5. The imaging system of claim 1, further including a tunable wavelength filter disposed between said second conduit and said focussing imaging detector to provide a selectively filtered optical image to said focussing imaging detector.

6. The imaging system of claim 5, wherein said tunable wavelength filter selectively provides one of a red and a non-red image to said focussing imaging detector.

7. The imaging system of claim 6, further comprising means for comparing said red and said non-red signal, and providing an indication of the presence of a disease condition of said selected imaging object.

8. The imaging system of claim 1, wherein said first and said second conduits comprise a fiber-optic probe having corresponding first and second portions, said second portion corresponding to said second conduit having an array of optical fibers.

9. The imaging system of claim 8, wherein said fiber-optic probe further includes an annular tube connected to a controllable vacuum for evacuating extraneous matter present in the region of the end of said probe.

10. The imaging system of claim 1, wherein said first conduit illuminates said selected imaging object, and said' second conduit receives an optical image from radiation transmitted through said selected imaging object.

11. The imaging system of claim 1, wherein said, second conduits comprises a plurality of second conduits adapted to provide a plurality of optical images to said focussing imaging detector from said selected imaging object.

12. The imaging system of claim 1, further including a image deflector connected to said second conduit to provide a selected plurality of images to said focussing imaging detector of said selected imaging object.

13. The imaging system of claim 1, further including an image processor connected to receive said output signal from said focussing image detector and provide a signal corresponding to an image representing said selected imaging object, said image processor further including blur-removal means for removing image artifacts caused by movement of at least said second conduit over said selected imaging object.

14. The imaging system of claim 1, wherein said focussing imaging detector comprises one of a FEBCCD and a EBCMOS detector.

15. The imaging system of claim 14 configured and disposed to provide an endoscopic imaging system.

16. The imaging system of claim 1, further comprising means for suppressing positive ion feedback.

17. A magnetically focussed image detector comprising:
   a photocathode disposed to receive photons and provide electrons corresponding to the intensity of the received photons;
   one of a CCD and a CMOS detector disposed a selected distance from said photocathode to receive said electrons;
   means for urging said electrons toward said one of a CCD and a CMOS detector from said photocathode; and
   a magnetic field source disposed to provide a magnetic field along said selected distance, wherein said electrons are caused to move in a helical path toward said one of a CCD and a CMOS detector of selected radius change.

18. The magnetically focussed image detector of claim 17, wherein the radius of curvature of said helical electron path is selected to decrease in proximity to the CCD or CMOS detector.

19. A reduced ion positive feedback detector comprising:
   one of a CCD and a CMOS detector disposed a selected distance from said means for providing electrons to receive said electrons;
   means for providing electrons to said one of said CCD and said CMOS detector along a path according to a selected signal;
   a magnetic field source disposed to provide a magnetic field along said selected distance, wherein said electrons are caused to move in a helical path toward said on of said CCD and said CMOS detector of selected radius change.

20. A method of eliminating positive ion feedback, comprising the steps of:
   applying electrons to one of a CCD and a CMOS detector along a first axis from a source; and
   applying a magnetic field along said first axis in vicinity of said one of said CCD and said CMOS detector, wherein ions generated by the impact of said electrons on the one of said CCD and said CMOS detector travel on a path divergent from said source and said first axis.

* * * * *